United States Patent [19]

Daniel et al.

[11] Patent Number: 4,608,149

[45] Date of Patent: Aug. 26, 1986

[54] POTASSIUM ION-SELECTIVE COMPOSITIONS AND ELECTRODES CONTAINING SAME

[75] Inventors: Daniel S. Daniel; Thomas R. Kissel, both of Rochester, N.Y.

[73] Assignee: Eastman Kodak Company, Rochester, N.Y.

[21] Appl. No.: 781,364

[22] Filed: Sep. 30, 1985

Related U.S. Application Data

[63] Continuation of Ser. No. 506,246, Jun. 20, 1983.

[51] Int. Cl.$^4$ .............................................. G01N 27/46
[52] U.S. Cl. .................................. 204/418; 204/1 T; 252/408.1
[58] Field of Search ............... 204/1 T, 1 A, 416, 418; 252/408.1

[56] References Cited

U.S. PATENT DOCUMENTS 4,276,141 6/1981 Hawkins ........................... 204/418
4,476,007 10/1984 Toner et al. ....................... 204/418

Primary Examiner—T. Tung
Attorney, Agent, or Firm—J. Lanny Tucker

[57] ABSTRACT

Potassium ion-selective compositions which comprise valinomycin and a particular carrier solvent capable of solvating valinomycin are disclosed. The carrier solvent is a dicarboxylic acid diester having at least 25 carbon atoms, a viscosity of less than about 120 centipoise at 20° C. and a boiling point greater than about 170° C. at 5 mm pressure. A preferred carrier solvent is diisodecyl phthalate. Membranes prepared from these compositions preferably have a glass transition temperature greater than about −50° C. These membranes are particularly useful in dry-operative potassium ion-selective electrodes which are capable of selectively determining potassium ions in preference to other ions.

16 Claims, 2 Drawing Figures

POTASSIUM ION-SELECTIVE COMPOSITIONS AND ELECTRODES CONTAINING SAME

The patent application is a continuation of U.S. Ser. No. 506,246 filed June 20, 1983.

FIELD OF THE INVENTION

This invention relates to compositions containing valinomycin which are useful as potassium ion-selective membranes. The compositions are useful in dry-operative ion-selective electrodes for selectively determining potassium ions in preference to other cations.

DESCRIPTION RELATIVE TO THE PRIOR ART

In the diagnosis and treatment of various diseases as well as in preventative health checkups, it is becoming increasingly important to monitor the concentrations of certain ions (e.g. cations) in a patient's body. One cation which has merited considerable attention is potassium. High serum potassium levels are known to cause changes in muscle irritability, respiration and myocardial functions. Low potassium levels can cause excitatory changes in muscle irritability and myocardial function. Therefore, serum potassium determination has become an important diagnostic tool when extremely high or low serum potassium levels are suspected.

One type of ion-selective electrode useful in determining ion concentration in body fluids has an electrode body (usually a glass or plastic container) containing a reference solution in contact with a half-cell of known potential (a reference electrode) and an ion-selective membrane located in an aperture in the electrode body. The ion-selective membrane is mounted in such a fashion that, when the electrode is immersed in the unknown solution, the membrane contacts both the reference and unknown solutions. A metal probe coated with a layer of insoluble salt of the metal in the reference solution and immersed therein serves as one of the contacts for measuring the potential between the electrodes and provides a reference potential for the electrode. The sensitivity of the electrode to an ion in solution is determined by the composition of the membrane. This type of electrode is referred to in the art as a "barrel" electrode.

The ion-selective membranes in barrel electrodes may be comprised of glass, solid salt precipitates or polymers. The polymeric membranes generally comprise a polymeric binder or support as the supporting matrix which is impregnated with a solution of an ion-selective carrier in a carrier solvent. The ion-selective carrier is a compound which is capable of sequentially complexing the desired ion and transporting the ion across the membrane-solution interface. This compound is also referred to in the art as an "ionophore" or "ion carrier". Depending upon the ionophore, solvent and binder, membranes of this type can be used to detect a particular ion preferentially to other ions which may be in the solution.

Carrier solvents useful in ion-selective membranes must exhibit certain properties. The carrier solvents must provide suitable ion mobility in the membranes, be compatible with the supporting matrix and be sufficiently hydrophilic to permit rapid wetting of the membrane by aqueous solutions but sufficiently water-insoluble to inhibit leaching out into those aqueous solutions. Ideally, they also plasticize the supporting matrix and are substantially nonvolatile, thereby providing extended shelf life for the membrane.

A significant advance in the ion-selective-electrode art is the dry-operative electrode described in U.S. Pat. No. 4,214,968 (issued July 29, 1980 to Battaglia et al). Prior to the discovery of such dry-operative ion-selective electrodes, electrodes had to be either stored in an aqueous solution or treated with aqueous solution just prior to use in an ion-activity-determining operation. The term "dry-operative" refers to an ion-selective electrode which provides reproducible potentiometric determination of ion activity which is related to the ion concentration of an aqueous test solution with no requirement for wet storage or preconditioning prior to use.

One of the specific ion-selective electrodes disclosed in the examples of Battaglia et al is a potassium ion-selective electrode using valinomycin as the potassium-selective ionophore dissolved in a variety of solvating compounds. Among useful solvents mentioned are phthalates, sebacates, aromatic and aliphatic ethers, phosphates, mixed aromatic aliphatic phosphates, adipates and mixtures thereof. In the potassium-selective electrodes utilizing valinomycin as the ionophore, particularly preferred carrier solvents disclosed are bromophenyl phenyl ether and certain trimellitates.

Dry-operative ion-selective electrodes are also described in Fuji's Japanese Patent Publication Nos. 17851/1982 and 17852/1982, both published Jan. 29, 1982. In the first example of each publication, a $K^+$-selective electrode containing valinomycin, poly(vinyl chloride) and dioctyl phthalate as the carrier solvent. However, it has been observed that an electrode prepared using dioctyl phthalate as the carrier solvent exhibited poor precision in potassium ion determinations under certain conditions of use.

Further, it has been found that potassium ion-selective membranes and electrodes containing the membranes which are prepared according to the teaching of the Battaglia et al patent using the preferred carrier solvents taught therein (e.g. triisodecyl trimellitate), also exhibit undesirably poor precision in potassium ion determinations under certain conditions of use. It has also been observed that such membranes and electrodes are often sensitive to ambient temperature fluctuations thereby worsening precision in assay results. This poor precision worsens with extended storage.

It has been further observed that the state of the art dry-operative potassium ion-selective electrodes often exhibit asymmetry potential. The asymmetry potential of an ion-selective membrane is an operationally-defined parameter relating to the cross-sectional uniformity of the membrane. It is the potential which is generated across the membrane when both of its sides are exposed to the same test sample. If the potential is other than zero, the membrane has compositional differences between its two sides, i.e. it is asymmetric.

Since asymmetry reflects a nonequilibrium state in the membrane, a relaxation or other change in the potential is often observed. If the change in the potential occurs at a slow enough rate that little change is seen during the time for ion measurement, the asymmetry can be calibrated out in ion determination calculations. This situation generally occurs for ion-selective glass membranes. However, if the asymmetry potential change is fast enough to occur during the time for ion determination, the precision results are adversely affected. This problem has frequently been observed in potassium ion-selective electrodes containing liquid carrier solvent membranes.

Asymmetry can sometimes be alleviated in certain electrodes by soaking the membrane several hours (18 or more) in a conditioning solution so that any large change in asymmetry potential can occur prior to its use in an ion determination. However, such a conditioning period is precluded for dry-operative ion-selective electrodes which would be detrimentally affected by wet storage or conditioning.

Hence, there is a need for a potassium ion-selective composition and dry-operative electrode containing same which have improved precision and are insensitive to fluctuations in ambient temperature. Further, there is a need for a potassium ion-selective membrane which exhibits little or no asymmetry potential, thereby improving assay precision.

SUMMARY OF THE INVENTION

In accordance with this invention, it has been found that certain ion-selective compositions and dry-operative electrodes containing same exhibit high selectivity for potassium ions over other cations in a sample specimen as well as unexpected improved precision in potassium ion determinations. In particular, it has been found that membranes prepared from ion-selective compositions containing valinomycin and a certain class of carrier solvents exhibit improved precision in results and less sensitivity to fluctuations in ambient temperature. Further, these compositions exhibit these improved properties over a long period of time and therefore have greater shelf life.

Another unexpected advantage observed with these compositions is their reduced tendency to form asymmetric membranes. This characteristic of the membranes also improves assay precision.

In accordance with this invention, there is provided a dry-operative potassium ion-selective electrode comprising valinomycin dissolved in a dicarboxylic acid diester capable of solvating valinomycin, such diester having at least 25 carbon atoms and a viscosity of less than about 120 centipoise at 20° C. and a boiling point greater than about 170° C. at 5 mm pressure. In a preferred embodiment, the valinomycin and diester are distributed within a supporting matrix, e.g. a hydrophobic polymer binder.

DETAILED DESCRIPTION OF THE INVENTION

Figure 1:
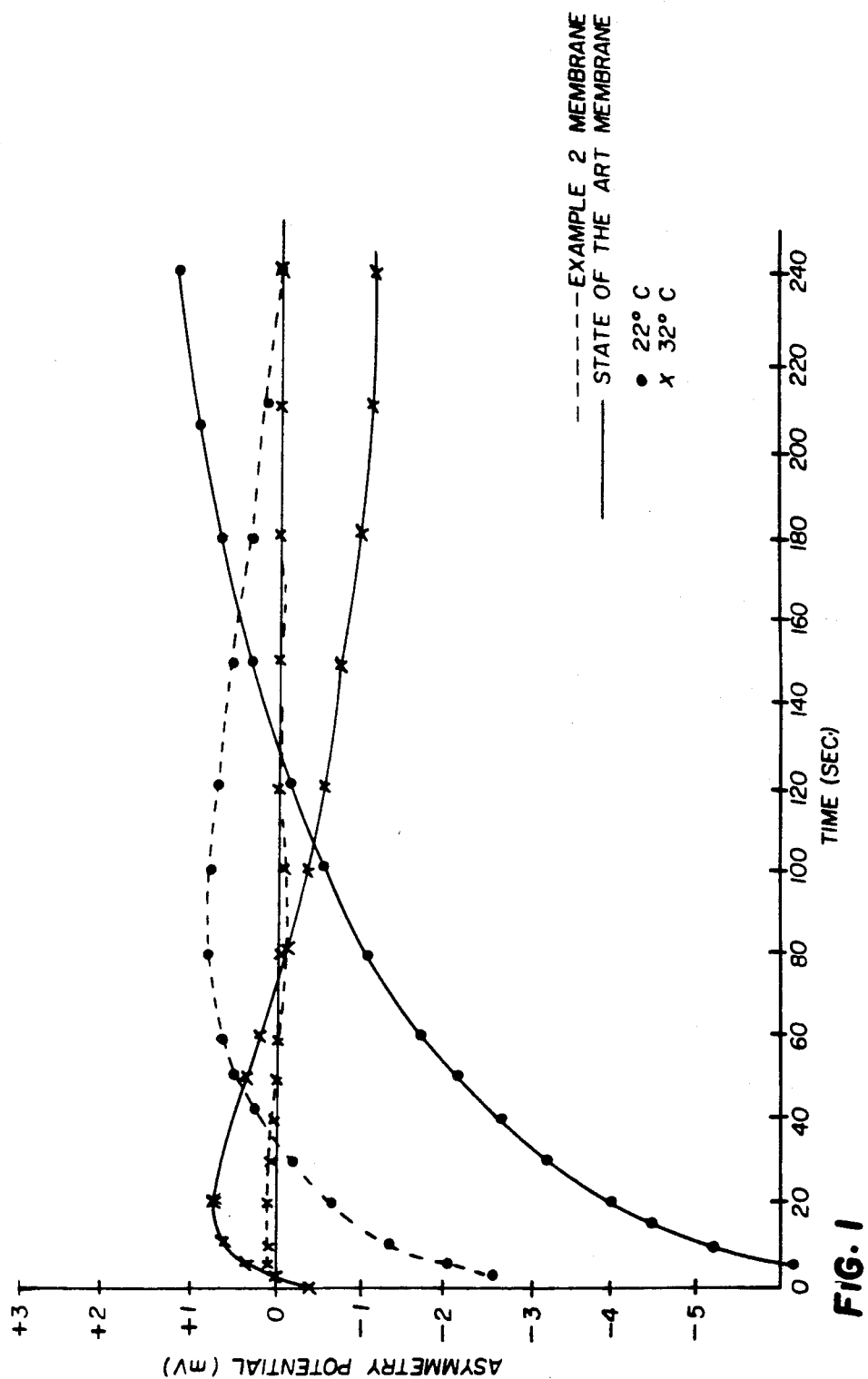
FIG. 1 is a graphical plot of asymmetry potential (mV) vs. time (sec.) for a membrane prepared according to this invention and for a state of the art membrane.

The potassium ion-selective compositions useful in the present invention include valinomycin as the ionophore. Valinomycin can be obtained commercially from a number of sources, including, for example, Calbiochem, located in LaJolla, Calif.

The valinomycin is solvated by one or more specific organic solvents described in more detail hereinbelow. These solvents are also known as carrier solvents. The supporting matrix can also solvate the ionophore, but a separate carrier solvent is also included in the compositions. The use of the supporting matrix is optional in some ion-selective electrodes. Such a matrix must allow for the transport of the potassium ions which are bound to valinomycin in the carrier solvent. For example, a porous glass support can be used as the supporting matrix. In those embodiments, valinomycin is dissolved in the carrier solvent and the resulting solution is imbibed into the porous glass support to provide an ion-selective membrane. In other and preferred embodiments, the solution of valinomycin is dispersed in a hydrophobic binder, e.g. a hydrophobic polymer binder. By "hydrophobic" is meant substantially water-insoluble. The binder dispersion is coated and dried to produce a potassium ion-selective membrane useful in the present invention.

The carrier solvent useful in the practice of this invention is a dicarboxylic acid diester capable of solvating valinomycin and having at least 25 carbon atoms and a viscosity of less than about 120 centipoise at 20° C. and a boiling point greater than about 170° C. at 5 mm pressure. Examples of such carrier solvents are sebacates, phthalates, adipates, suberates, azelates, glutarates, succinates and hexahydrophthalates which have the noted carbon atom, viscosity and boiling point characteristics. Preferably, the carrier solvent is a sebacate, phthalate and adipate. More preferably, it is a phthalate. Examples of useful carrier solvents are listed in Table 1 below:

TABLE I

| Solvent | Viscosity (cp at 20° C. | b.p. (at 5 mm) |
| --- | --- | --- |
| diisodecyl phthalate | 94 | 233 |
| bis(2-ethylhexyl) sebacate | 21 | 187 |
| diisodecyl adipate | 18 | 220 |

A particularly preferred composition includes valinomycin and diisodecyl phthalate as the carrier solvent.

These carrier solvents are all commercially available. For example, diisodecyl phthalate is available from Ashland Chemical Co., Buffalo, N.Y.

A membrane composition can be formed by incorporating the carrier solvent and valinomycin in one or more binders which serve as the supporting matrix. Useful binders include hydrophobic natural or synthetic polymers capable of forming thin films of sufficient permeability to produce, in combination with the valinomycin and carrier solvent, ionic mobility across the membrane interfaces. Useful polymers include poly(vinyl chloride); poly(vinylidene chloride); poly(acrylonitrile); polyurethanes, particularly aromatic polyurethanes; copolymers of vinyl chloride and vinylidene chloride; poly(vinyl butyral); poly(vinyl formal); poly(vinyl acetate); copolymers of vinyl acetate and vinyl chloride; silicone elastomers; and copolymers of vinyl alcohol, cellulose esters and polycarbonates. Other useful polymers include carboxylated polymers of poly(vinyl chloride) and mixtures and copolymers of these materials. A preferred binder is poly(vinyl chloride-co-vinyl acetate) (90:10 weight ratio). Membranes including one or more binders, valinomycin and one or more of the described carrier solvents are prepared using conventional film-coating or casting techniques.

The membranes useful in this invention preferably have a glass transition temperature (Tg) of greater than about −50° C. in order to have desired film characteristics. Tg can be determined by any convenient method suitable for this purpose. For example, one such method is differential scanning calorimetry, as described in *Techniques and Methods of Polymer Evaluation*, Vol. 2, Marcel Dekker, Inc., N.Y. 1970. Preferably, the membranes have a Tg in the range of from about −50 to about −20° C.

The membranes useful in the present invention contain the described components over a wide range of concentrations or coverages. The coverage of valinomycin depends upon the carrier solvent used, as well as other factors. The preferred membranes comprise a hydrophobic binder having the carrier solvent and valinomycin dispersed therein. In those membranes, valinomycin coverages of between about 0.1 $g/m^2$ and 2.0 $g/m^2$ are useful and coverages between about 0.2 $g/m^2$ and 0.8 $g/m^2$ are preferred.

The carrier solvent is present in an amount sufficient to solvate valinomycin. The amount therefore depends on the particular solvent chosen. Generally, more solvent is used than is necessary to solvate valinomycin so that it remains solvated under a variety of storage conditions. A 100 to 500 percent excess on a weight basis is particularly useful. Usually, the coverage of carrier solvent will be within the range of from about 2 $g/m^2$ to about 24 $g/m^2$, and preferably from about 5 to about 20 $g/m^2$.

The amount of hydrophobic binder which is present is determined by the desired thickness of the membrane and by the necessity for providing support for the valinomycin-solvent dispersion. The membranes generally have a thickness in the range of from about 2 μm to about 20 μm. The binder coverage is usually between about 2 and 24, and preferably from about 3 to about 12 $g/m^2$.

In addition to the binder, valinomycin and carrier solvent, the described membrane compositions optionally contain other components such as surfactants and plasticizers in amounts known to those skilled in the art.

As noted, surfactants are useful components of the described membranes. The surfactants serve a variety of functions including improving the coatability of the membrane composition and improving the solvation of valinomycin by the binder or carrier solvent. Useful surfactants include nonionic surfactants such as the alkylaryl polyether alcohols (Tritons ™) available from Rohm and Haas Co; (p-isononylphenoxy)-polyglycidol (Surfactant 10G ™) available from Olin Mathieson Corp; polyoxyethylene (20) oleyl ether (Brij 98 ™), polyoxyethylene sorbitan monolaurate (Tween 20 ™) and Span 80 ™, all available from Atlas Chemical Industries; poly(dimethyl-comethylphenyl siloxane) (DC-510 ™) available from Dow Corning; Zonyl FSN ™ available from E. I. duPont; and fluorochemical surfactant FC134 ™ available from 3M Co.

The described membranes are useful in a variety of dry-operative electrode structures including, for example, the dry ion-selective electrodes described in Japanese Patent Publication Nos. 17851/1982 and 17852/1982, both published Jan. 29, 1982 noted hereinabove.

In a particularly preferred embodiment, the described membranes are used in a dry-operative ion-selective electrode as described in U.S. Pat. No. 4,214,968 noted hereinabove. In this embodiment, there is provided a dry-operative ion-selective electrode comprising:

(a) a dried internal reference element comprising the dried residue of a solution of a salt and a hydrophilic polymeric binder in a solvent for the polymer and the salt and, (b) in physical contact with the reference element, a hydrophobic ion-selective membrane of predetermined uniform thickness in regions thereof intended for physical contact with the sample for analysis, the membrane comprising a hydrophobic binder having distributed therein valinomycin dissolved in the diester carrier solvent described hereinabove.

In this embodiment of the present invention, the electrodes are made by a process and using components which are described in U.S. Pat. No. 4,214,968 (noted hereinabove), the disclosure of which is hereby incorporated by reference in its entirety. As used throughout this specification and in the claims, the expressions "dry-operative", "dried" and "uniform" have the meanings defined in that patent. The use of the hydrophilic binder in the dried internal reference element is optional, but preferred.

The electrodes of this invention can be used to determine the concentration of potassium in an aqueous solution, e.g. biological fluids such as whole blood, intracellular fluids, blood sera and urine. Generally, a portion of the solution to be assayed is brought into contact with the dry-operative ion-selective electrode described hereinabove which is capable of making potentiometric measurements related to the potassium ion concentration. Subsequently, the difference in potential between the portion of aqueous solution and the reference electrode is measured. Preferably, a drop of tne aqueous solution is spotted onto the potassium ion-selective membrane of such electrode with a pipette or other suitable means, but other ways of contacting the electrode with the solution are acceptable.

The following examples are presented to illustrate the practice of this invention.

The dry-operative electrodes used in these examples were of the format and prepared by the methods described by the Battaglia et al patent referenced hereinabove. In general, each electrode comprised a polyester support having layers in sequence as follows: silver/silver chloride reference electrode; electrolyte layer comprising gelatin (3–6 $g/m^2$), NaCl (1.5–3.5 $g/m^2$), glycerol (0.25–0.4 $g/m^2$) and Olin Surfactant 10G ™ (0.3–0.9 $g/m^2$); and the membrane layer.

The membrane layer contained: poly(vinyl chloride-co-vinyl acetate) (90:10 weight ratio) as supporting matrix (3.0–12.0 $g/m^2$), a carrier solvent as indicated (12–16 $g/m^2$), valinomycin (0.2–0.8 $g/m^2$), and the surfactant DC-510 ™ (0.03–0.15 $g/m^2$).

EXAMPLE 1

Potassium Ion-Selective Electrode Using Diisodecyl Phthalate As Carrier Solvent Having Improved Precision This is a comparative example illustrating the improved precision of the dry-operative potassium ion-selective electrode of this invention compared to a state of the art dry-operative potassium ion-selective electrode described in U.S. Pat. No. 4,214,968 (Battaglia et al) noted hereinabove.

The electrodes were tested by spotting 10 μL aliquots of the sample specimen indicated and potentials were measured against a reference electrode consisting of an identical piece of potassium electrode which was spotted with 10 μL of a standard saline reference solution.

The potentials were evaluated using an EKTACHEM TM E-400 clinical analyzer available from Eastman Kodak Co., Rochester, N.Y. The potentials were measured for several electrodes for each sample specimen and standard deviations ($\sigma$mV) of millivolt readings were determined.

In tests 1 and 2, the sample specimens tested were "serum" samples obtained from 2 serum-based calibrators and a serum pool, and "saline" samples which were from a solution of 0.1 M KCl and poly(vinyl pyrrolidone) (5 g/L) in water. Twenty-seven "serum" replicates and nine "saline" replicates were performed. In tests 3 and 4, one hundred and fifty "serum" replicates were obtained from three serum control fluids. In each test, the mV potentials were calculated using the K+ concentration data obtained from the EKTACHEM TM analyzer at two different ambient temperatures ($\approx$20° C. and $\approx$30° C.), and the standard deviations ($\sigma$mV) were determined. The reference fluid in each test was a protein-free physiological saline solution containing 5 g/L poly(vinyl pyrrolidone), 140mM Na+, 4.5 mM K+, 108 mM Cl− and 25 mM $HCO_3^-$ at pH 9.

The resulting data are presented in Table II. The lower the $\sigma$mV value, the more precise is the electrode in measuring K+. The state of the art electrodes were prepared using triisodecyl trimellitate (360 cps viscosity; >170° C. b.p. at 5 mm) as carrier solvent. The electrodes of this invention were prepared using diisodecyl phthalate as the carrier solvent.

TABLE II

| Test | Electrode | Sample Specimen | $\sigma$mV (20° C.) | $\sigma$mV (30° C.) |
|---|---|---|---|---|
| 1 | Control | "serum" | 0.32 | 0.57 |
|   | " | "saline" | 0.25 | 0.77 |
|   | Example | "serum" | 0.20 | 0.31 |
|   | " | "saline" | 0.21 | 0.28 |
| 2 | Control | "serum" | 0.31 | 0.58 |
|   | " | "saline" | 0.28 | 0.58 |
|   | Example | "serum" | 0.22 | 0.17 |
|   | " | "saline" | 0.25 | 0.13 |
| 3 | Control | "serum" | 0.33 | 0.38 |
|   | Example | "serum" | 0.26 | 0.23 |
| 4 | Control | "serum" | 0.32 | 0.66 |
|   | Example | "serum" | 0.23 | 0.27 |

As can be seen from these data, the electrodes of the present invention exhibit improved precision in assay results over the state of the art electrodes. This improvement is particularly pronounced at the higher ambient temperature.

EXAMPLE 2

Potassium Ion-Selective Electrode Having Reduced Asymmetry Potential

This is a comparative example illustrating the reduced asymmetry potential exhibited by a potassium ion-selective membrane prepared according to this invention compared to a state of the art potassium ion-selective electrode.

Two dry-operative ion-selective electrodes (a control and an example) were prepared by the procedure described in Example 1. Following electrode preparation, each membrane was peeled off its respective electrode and supported in the center of a plexiglass concentration cell so as to form a barrier between two 40 mL compartments of the cell. An anodized Ag/AgCl wire was placed in each compartment for use as a measurement electrode. About 10 mL f the physiological saline solution noted in Example 1 was placed the bottom of each cell compartment so as to wet the electrodes but not the membrane. Three minutes after this addition, an additional 30 mL of saline solution was added to each compartment and the asymmetry potential was measured with the electrodes. The saline solutions were at either 22° C. or 32° C. A fresh piece of membrane was used for each test. The resulting data were plotted in graphical form as illustrated in FIG. 1. As an ideal, it is desirable that the asymmetry potential be as close to zero as possible. This figure indicates that the absolute magnitude of the asymmetry potential is considerably less for the membrane of this invention than for a state of the art membrane. Further, the change in asymmetry potential caused by the higher ambient temperature (32° C.) is less for the membrane of this invention than for the state of the art membrane.

EXAMPLE 3

Potassium Ion-Selective Electrode Having Improved Temperature Stability

This is a comparative example illustrating the improved temperature stability exhibited by a potassium ion-selective electrode of this invention compared to a state of the art potassium ion-selective electrode.

Both electrodes (control and example) were prepared by the procedure described in Example 1 except that the example electrodes contained 16 g/m² of diisodecyl phthalate as the carrier solvent and the control electrode contained 12 g/m² of triisodecyl trimellitate.

Figure 2:
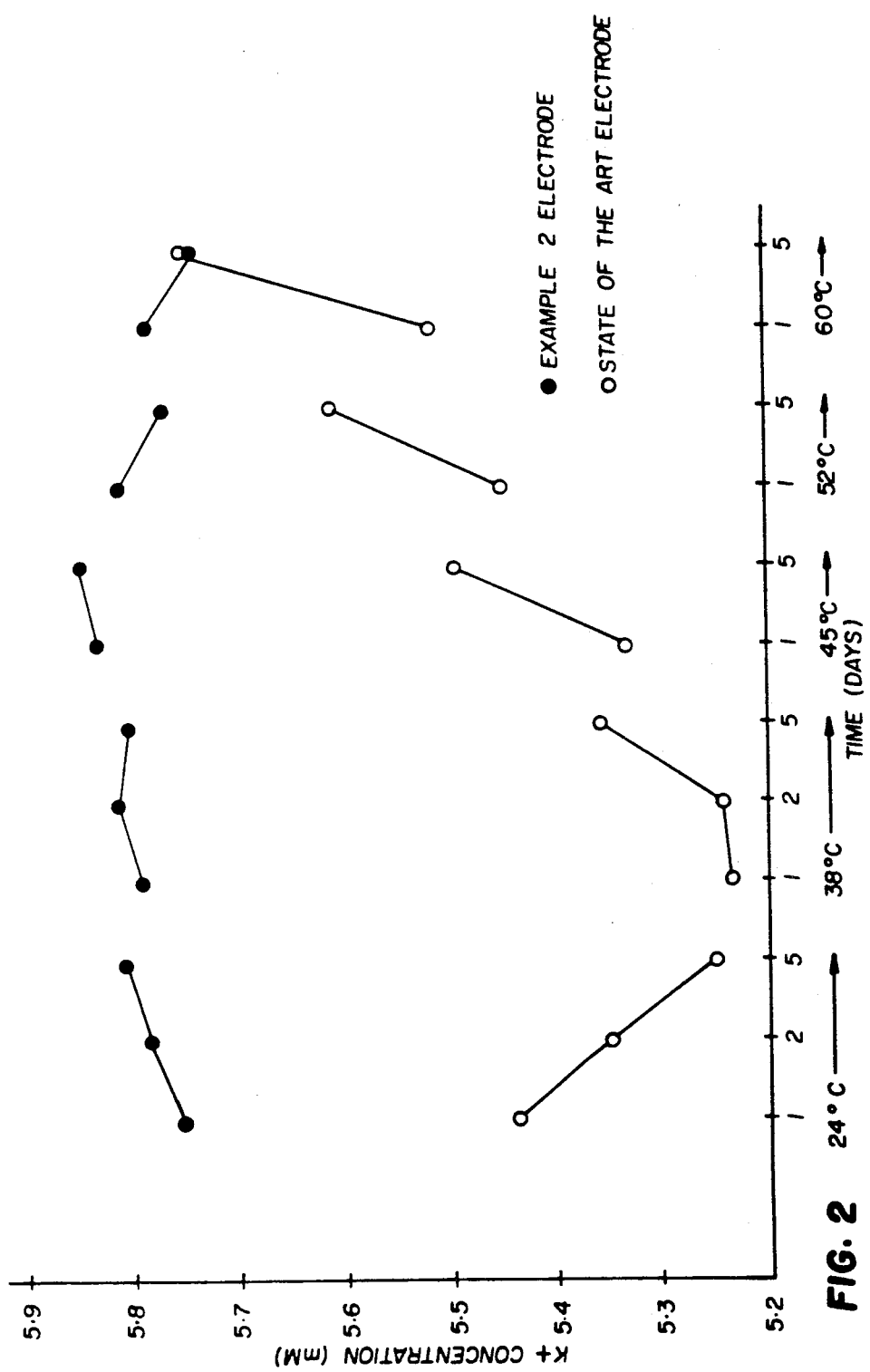
FIG. 2 is a graphical plot of potassium ion concentration (mM) vs. time (days) at various keeping temperatures for an electrode of this invention and a state of the art electrode.

The electrodes were subjected to various keeping or storage temperatures (24° C., 38° C., 45° C., 52° C. and 60° C.) under conventional accelerated keeping conditions and frozen until tested. Each electrode was then tested for K+ concentration at 70° C. and 50% relative humidity using a commercially-available pooled bovine serum as a source of specimen samples. The results of these tests are illustrated in FIG. 2. The data in that figure show the improved temperature stability exhibited by the electrodes of this invention over state of the art electrodes at all keeping temperatures considered. The electrodes of this invention show little change in K+ determination after storage for up to five days while the state of the art electrodes show considerable change.

The invention has been described in detail with particular reference to preferred embodiments thereof, but it will be understood that variations and modifications can be effected within the spirit and scope of the invention.

We claim:

1. A potassium ion-selective composition comprising valinomycin and diisodecyl phthalate.

2. The composition of claim 1 comprising a surfactant.

3. The composition of claim 1 comprising a hydrophobic polymer binder.

4. A potassium ion-selective composition comprising valinomycin, diisodecyl phthalate and poly(vinyl chloride-co-vinyl acetate).

5. A dry-operative potassium ion-selective electrode comprising valinomycin dissolved in a dicarboxylic acid diester capable of solvating valinomycin, said diester having at least 25 carbon atoms, a viscosity of less than about 120 centipoise at 20° C. and a boiling point greater than about 170° C. at 5 mm pressure.

6. The electrode of claim 5 wherein said valinomycin and said diester are distributed within a hydrophobic polymer binder.

7. A dry-operative potassium ion-selective electrode comprising:
   (a) a dried internal reference element comprising the dried residue of a solution of a salt and a hydrophilic polymeric binder in a solvent for the polymer and the salt and,
   (b) in physical contact with said reference element, a hydrophobic ion-selective membrane of predetermined uniform thickness in regions thereof intended for physical contact with a sample for analysis, the membrane comprising a hydrophobic polymeric binder having distributed therein valinomycin dissolved in a sebacate, phthalate or adipate capable of solvating valinomycin and having at least 25 carbon atoms, a viscosity less than about 120 centipoise at 20° C. and a boiling point greater than about 170° C. at 5 mm pressure.

8. The electrode of claim 7 wherein said membrane has a glass transition temperature greater than about −50° C.

9. The electrode of claim 8 wherein said diester is a phthalate.

10. The electrode of claim 9 wherein said diester is diisodecyl phthalate.

11. The electrode of claim 7 wherein said membrane comprises a surfactant.

12. A dry operative potassium ion-selective electrode comprising:
    (a) a dried internal reference element comprising the dried residue of a solution of a salt and a hydrophilic polymeric binder in a solvent for the polymer and the salt and,
    (b) in physical contact with said reference element, a hydrophobic ion-selective membrane of predetermined uniform thickness in regions thereof intended for physical contact with a sample for analysis, the membrane having a glass transition temperature of greater than about −50° C. and comprising poly(vinyl chloride-co-vinyl alcohol) having distributed therein valinomycin dissolved in diisodecyl phthalate.

13. A potassium ion-selective composition comprising valinomycin and a carrier solvent selected from the group consisting of diisodecyl phthalate, bis(2-ethylhexyl) sebacate and diisodecyl adipate.

14. A dry-operative potassium ion-selective electrode comprising valinomycin dissolved in a carrier solvent selected from the group consisting of diisodecyl phthalate, bis(2-ethylhexyl) sebacate and diisodecyl adipate.

15. The electrode of claim 14 wherein said valinomycin and carrier solvent are distributed within a hydrophobic binder.

16. The electrode of claim 15 wherein said hydrophobic binder is poly(vinyl chloride-co-vinyl acetate).

* * * * *